United States Patent [19]

Suzuki et al.

[11] 4,388,166
[45] Jun. 14, 1983

[54] ELECTROCHEMICAL MEASURING APPARATUS PROVIDED WITH AN ENZYME ELECTRODE

[75] Inventors: Shuichi Suzuki; Masuo Aizawa, both of Tokyo; Masao Koyama, Yokohama; Yuichi Sato, Atsugi; Junji Koezuka, Yokohama, all of Japan

[73] Assignee: Tokyo Shibaura Denki Kabushiki Kaisha, Kawasaki, Japan

[21] Appl. No.: 357,811

[22] Filed: May 15, 1982

Related U.S. Application Data

[63] Continuation of Ser. No. 175,038, Aug. 4, 1980, abandoned.

[30] Foreign Application Priority Data

Aug. 14, 1979 [JP] Japan ................................ 54-102761

[51] Int. Cl.³ ............................................. C12Q 1/26
[52] U.S. Cl. .................................... 204/403; 204/415; 435/817
[58] Field of Search ............... 204/195 P, 195 B, 1 E; 435/817; 128/635

[56] References Cited

U.S. PATENT DOCUMENTS

| | | | |
|---|---|---|---|
| 3,948,745 | 4/1976 | Guilbault et al. | 204/195 B |
| 3,954,925 | 5/1976 | Boddeker | 264/41 |
| 3,979,274 | 9/1976 | Newman | 204/195 B |
| 4,005,002 | 1/1977 | Racine et al. | 204/195 P |
| 4,073,713 | 2/1978 | Newman | 204/195 B |
| 4,240,889 | 12/1980 | Yoda et al. | 204/195 B |

FOREIGN PATENT DOCUMENTS

| | | | |
|---|---|---|---|
| 2152219 | 4/1973 | France | 204/403 |
| 51-55691 | 9/1976 | Japan. | |
| 55-98347 | 7/1980 | Japan | 204/415 |
| 1442303 | 7/1976 | United Kingdom | 204/1 E |

OTHER PUBLICATIONS

Chemical Abstracts, vol. 93 (1980), Abstract 234558k.

*Primary Examiner*—G. L. Kaplan
*Attorney, Agent, or Firm*—Oblon, Fisher, Spivak, McClelland & Maier

[57] ABSTRACT

An electrochemical measuring apparatus which essemtially comprises an asymmetric semipermeable membrane mounted on an immobilized enzyme membrane of an enzyme electrode, said asymmetric semipermeable membrane being essentially formed of a thin semipermeable layer exposed to the outside for contact with a liquid to be measured and an inner adjacent thick porous layers, and can measure an organic ingredient such as glucose contained in blood or serum with high sensitivity in a short time and moreover has a prominent durability.

7 Claims, 7 Drawing Figures

LONG-TERM STABILITY

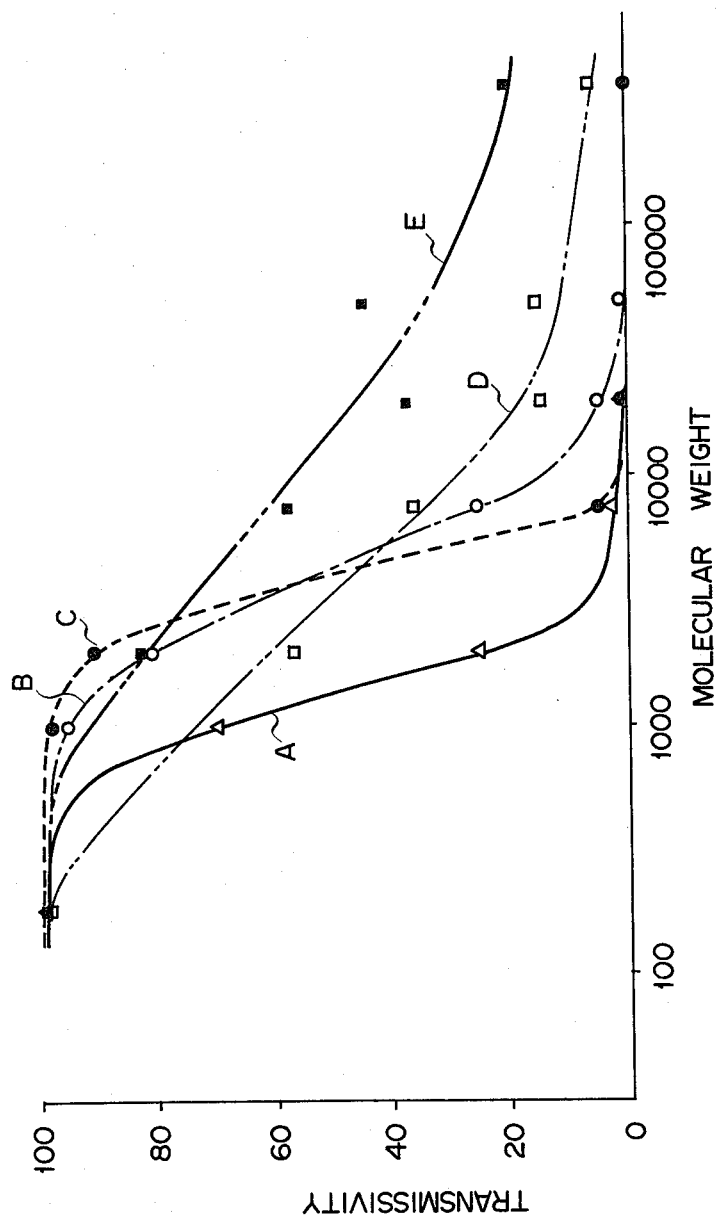

ELECTROCHEMICAL MEASURING APPARATUS PROVIDED WITH AN ENZYME ELECTRODE

This is a continuation of application Ser. No. 175,038, filed Aug. 4, 1980 and now abandoned.

This invention relates to an electrochemical measuring apparatus provided with an improved enzyme electrode.

Various electrochemical measuring apparatus provided with an enzyme electrode to easily determine the concentration of an organic ingredient contained in a liquid are known. Such electrochemical measuring apparatus are applied not only in the analysis of organic ingredients but also in the fields of medical diagnosis and treatment, biochemistry and the foodstuff industry.

The U.S. Pat. No. 3,539,455 to Clark, U.S. Pat. No. 3,948,745 to Guilbault et al, U.S. Pat. No. 4,005,002 to Racine et al, and U.S. Pat. Nos. 3,979,274 and 4,073,713 to Newman set forth electrochemical measuring apparatus and/or an enzyme electrodes applied thereto.

An enzyme electrode used with conventional electrochemical measuring apparatus comprises a galvanic cell type or polarographic electrode, enzyme membrane deposited on the sensitized plane of said electrode, and, in some cases, a semipermeable membrane covering said enzyme membrane. The conventional semipermeable membrane has a symmetric pore arrangement and is formed of, for example, reproduced cellulose or polycarbonate.

In the prior art electrochemical measuring apparatus, an enzyme electrode provided with a semipermeable, membrane indeed allows for a stable measurement, but the measurement takes a long time due to slow response. On the other hand, an enzyme electrode free of a semipermeable membrane makes a quick response, but has the drawback that measurement is accompanied with noise, resulting in noticeable variations in the measured values. Whether provided with the semipermeable membrane or not, the known enzyme electrode has the drawback that it loses stability during lengthy application. In other words, though stably applicable in a clear aqueous solution, such as an aqueous solution of glucose, the prior art enzyme electrode has the drawback that where measurement is made of the content of an organic ingredient such as glucose in a liquid such as blood, serum or urine, a high molecular material such as protein contained in such liquid tends to be noticeably deposited on the enzyme electrode, giving rise to a quick decline in the sensitivity, response speed and durability of said enzyme electrode, and consequently making it necessary to carry out frequent washings or replacements of the enzyme electrode.

At present, therefore, there is a demand in not only the field of chemical analysis but also the field of medical treatment and diagnosis to develop an electrochemical measuring apparatus provided with an enzyme electrode which can carry out quick, easy and stable measurements.

It is accordingly the object of this invention to provide an electrochemical measuring apparatus provided with an improved enzyme electrode which is increased in sensitivity and response speed, accompanied by little noise and stably applicable for a long period of time.

To attain the above-mentioned object, this invention provides an electrochemical measuring apparatus provided with an enzyme electrode which comprises:

an electrode whose outer end is provided with a sensitized plane;

an immobilized enzyme membrane deposited on said sensitized plane; and an asymmetric semipermeable membrane mounted on said immobilized enzyme membrane, and wherein said asymmetric semipermeable membrane is essentially formed of a thin semipermeable layer exposed to the outside for contact with a liquid, whose organic content is to be measured, and a thick porous layer inside of said thin semipermeable layer.

The asymmetric semipermeable membrane may be an integral material in which the fine pores of a thin semipermeable layer are stacked adjacent to the coarse pores of a thick porous layer in the direction of the thickness of said asymmetric semipermeable membrane. Or it is possible to separately fabricate said porous layer and semipermeable layer, and superpose said porous layer on said semipermeable layer, such that said semipermeable layer is exposed to the outside.

As used in this invention, the asymmetric semipermeable membrane is preferred to be impervious to more than 80% of a material having a molecular weight of 20,000 and permeable to more than 70% of a material having a molecular weight of 1,000. Most of the high molecular interfering materials such as protein which are deposited on an enzyme electrode to decrease its property or suppress the activity of the immobilized enzyme electrode itself have a larger molecular weight than 20,000. Those interfering materials are rejected by the asymmetric semipermeable membrane. Only a low molecular weight material such as glucose whose content is to be determined is allowed to pass through said asymmetric semipermeable membrane. Therefore, determination using said asymmetric semipermeable membrane is accompanied by less noise, indicates no variations in the results obtained and ensures stable high precision. The thick porous layer of the asymmetric semipermeable membrane has considerably larger pores than that of the thin semipermeable layer. Therefore, a material whose content is to be determined can quickly permeate through the porous layer, ensuring extremely high sensitivity and response speed of the enzyme electrode as a whole. This invention has the advantages that it is possible to reduce noise occurring in the enzyme electrode to an extent of ½ to 1/20 of that which has accompanied the conventional enzyme electrode free from the aforesaid asymmetric semipermeable membrane, and determinations can be made of a far lower concentration of an organic ingredient in a liquid than has been possible in the past. With the electrochemical measuring apparatus of this invention, noise occurring in the enzyme electrode is so low that it is unnecessary to try to decrease such noise particularly by applying an amplifier as is the case with the conventional electrochemical measuring apparatus whose enzyme electrode lacks the aforesaid asymmetric semipermeable membrane. Therefore, the electrochemical measuring apparatus of the invention has a very much simplified arrangement due to involvement of a fewer number of parts, and displays higher reliability.

Further, where measurement is made of the concentration of an organic material remaining, for example, in blood or sewage and containing protein having a molecular weight of scores of thousands to several millions of unit, then the enzyme electrode of this invention protected by the previously described asymmetric semipermeable membrane is prevented from being directly brought into contact with a material having such a large molecular weight as contaminates or damages the enzyme electrode. Therefore the electrochemical measuring apparatus of the invention is effectively saved from a decline in the property resulting from, for example, the deposition of a high molecular weight material. The electrochemical measuring apparatus of this invention has the advantages that stable determinations can be carried out without reduction in sensitivity and responsiveness and also substantially without obstruction by noise; the sensitized portion of the enzyme electrode can be effectively saved from damage which might result from the contact of said sensitized portion with any other mechanical part during measurement; even if damage arises due to such contact, the subject electrochemical measuring apparatus can be applied again simply by replacing the asymmetric semipermeable membrane; and if a decline is likely to take place in the property of the subject electrochemical measuring apparatus for a short time due to the drying of the sensitized portion of the enzyme electrode or the immobilized enzyme membrane mounted on said sensitized portion, such drying can be prevented by the water-holding property of the asymmetric semipermeable membrane.

The reason is not quite clear why the occurrence of noise is reduced in the electrochemical measuring apparatus of this invention. Yet it is assumed that the application of an asymmetric semipermeable membrane embodying this invention suppresses the irregular diffusion of an object to be determined through a liquid while it is being stirred, thereby ensuring the uniform diffusion of said object to be determined toward the enzyme electrode.

Figure 4:
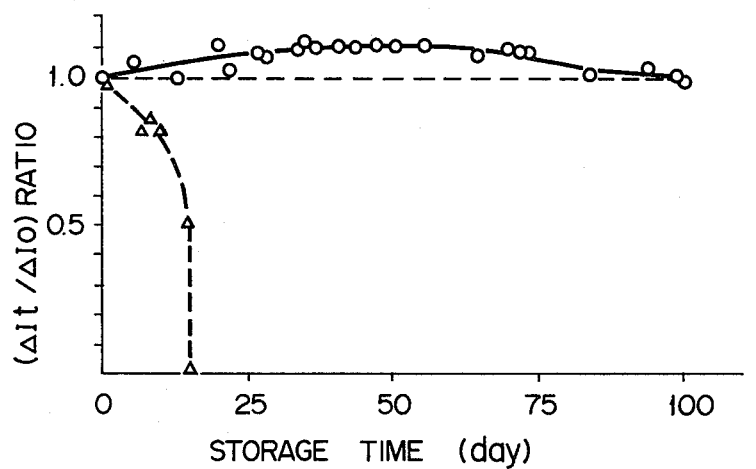

FIG. 3 graphically shows the permeability of an asymmetric semipermeable membrane used with the enzyme electrode of the invention; and FIG. 4 graphically shows the long term stability of the enzyme electrode of the present invention and that of the prior art enzyme electrode.

Figure 1A:
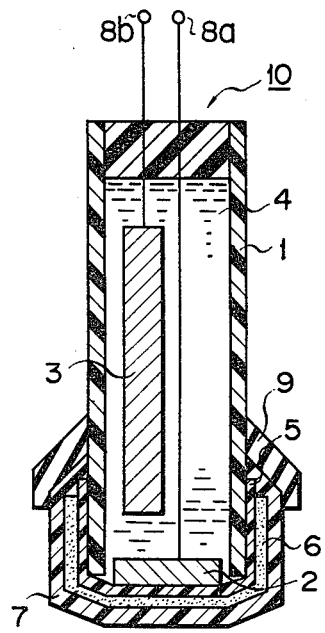
FIGS. 1A, 1B, 1C and 1D are sectional views of various enzyme electrodes used with an electrochemical measuring apparatus embodying this invention.

The electrode section (for example, Oxygen electrode) of the enzyme electrode 10 essentially comprises, as shown in FIG. 1A, an electrode cylinder 1 made of an insulation material such as glass or plastics material, cathode 2, anode 3, electrolyte 4 filled in the electrode cylinder 1 so as to be set between the cathode 2 and anode 3 and filter membrane 5 which is disposed close to the cathode 2 and constitute a sensitized plane. Both cathode 2 and anode 3 are connected to a current-measuring circuit (not show) by leads 8a, 8b. The oxygen electrode is rendered sensitive to oxygen (a material of detection) consumed or produced by the reaction of enzyme. With the embodiment of this invention, the electrode section may be a galvanic type whose cathode 2 is made of a noble metal such as platinum or gold, and whose anode 3 is formed of aluminium or lead. However, it is possible to apply a polarographic electrode section whose anode is prepared from silver/silver chloride and whose cathode is made of platinum or gold. FIG. 1A indicates an electrode section acting as an oxygen electrode. However, said electrode section may be constituted, if necessary, by a hydrogen peroxide electrode for detecting hydrogen peroxide, carbon dioxide electrode for detecting carbon dioxide, hydrogen ion electrode for detecting hydrogen ion, or any of the known various electrodes for detecting cyanogen ion, iodide ion, ammonia and monovalent ion.

Figure 1B:
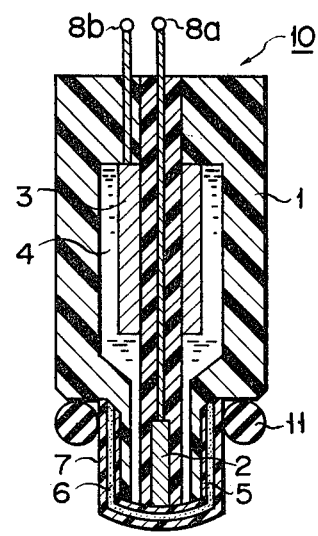
Figure 1C:
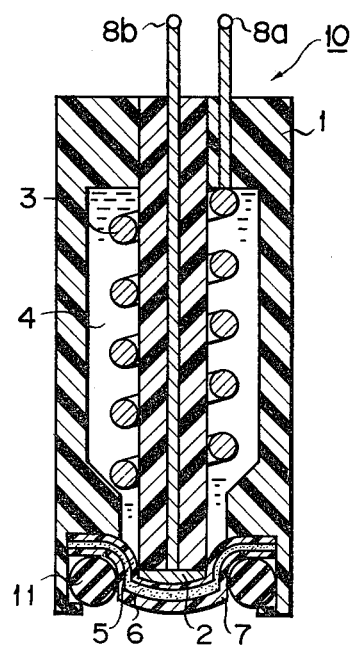
Figure 1D:
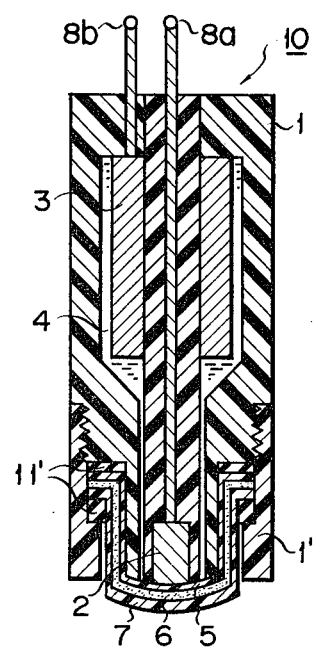

FIGS. 1B, 1C, and 1D show the modifications of an enzyme electrode 10 embodying this invention. In FIGS. 1B and 1C, an O-ring 11 is provided, and an immobilized enzyme membrane 6 and asymmetric semipermeable layer 7 are rendered detachable. The O-ring 11 of FIG. 1B concurrently acts as a sealing member in fixing the enzyme electrode 10. In FIG. 1D, a rubber packing 11′ is provided. The outer end portion 1′ is made detachable by threaded engagement with the electrode cylinder 1. The release of the outer end portion 1′ facilitates the replacement of the immobilized enzyme membrane 6 and asymmetric semipermeable membrane 7.

The filter membrane 5 is permeable to a material of detection and impervious to a material having a larger molecular weight or larger particle size than the material of detection. Various filter membranes an already set forth in the U.S. Pat. Nos. 3,539,455 and 3,979,274 and are easy of selection for those skilled in the art. Where the electrode section is constituted by an oxygen electrode, then it is possible to use a material impervious to water and electrolyte but permeable to oxygen gas, such as tetrafluoroethylene, fluoroethylene propylene, and polyethylene. When the electrode section is constituted by a hydrogen peroxide electrode, then it is possible to apply, for example, cellulose acetate, silicone rubber and methyl methacrylate. The filter membrane 5 is preferred to have a thickness of 6 to 12 microns. If the filter membrane 5 is too thick, then the resultant electrochemical measuring apparatus consumes a long time in making a response. On the other hand a too thin filter membrane decreases in mechanical strength. The filter membrane 5 is attached to the electrode cylinder 1 close to the cathode 2 with the electrolyte 4 disposed between said filter membrane 5 and cathode 2.

The immobilized enzyme membrane 6 is a membranous material used to fix enzyme on a substrate chemically or physically in order to prevent the efflux of enzyme. Such immobilized enzyme membrane is already known to those skilled in the art, and disclosed in the U.S. Pat. Nos. 3,539,455 and 3,948,745 description thereof being omitted. However, said immobilized enzyme membrane 6 should at least have such a structure as allows a material such as oxygen or glucose required for the reaction of enzyme to be conducted to the enzyme disposed in and on said membrane 6.

An organic ingredient to be measured is decomposed by the reaction of the enzyme used in this invention, thereby producing or consuming a material of detection such as oxygen, hydrogen peroxide, hydrogen and the like. Where the electrode section is constituted by, for example, an oxygen electrode, it is possible to apply enzymes such as alcohol oxidase, glucose oxidase, lactate oxidase, galactose oxidase, aldehyde oxidase, pyruvate oxidase, L-amino acid oxidase, NADH oxidase, ureido oxidase, ascorbate oxidase and catalase.

The asymmetric semipermeable membrane 7 is formed of a thin semipermeable layer and thick porous layer having large pores. The thick porous layer contacts the immobilized enzyme membrane 6, and the thin semipermeable layer is exposed to the outside for contact with a liquid whose organic content is to be determined. The thin semipermeable layer should preferably be as thin as possible. With the technique of the present day, said semipermeable layer can be thinned to an extent of several hundred Ångström units. The thicker the semipermeable layer the slower the rate at which an organic material such as glucose to be measured permeates said layer, and consequently the longer the time requires for the resultant electrochemical measuring apparatus to make a response. Therefore, said semipermeable layer is preferred to have a thickness of 1 micron at maximum, and further be formed of pores having a smaller diameter than 0.05 micron.

On the other hand, the thick porous layer having larger pores allows for the easy diffusion of an organic material such as glucose. Therefore, this porous layer can be made appreciably thicker for the purpose of imparting mechanical strength to the asymmetric semipermeable membrane and reducing the effect resulting from the agitation of a liquid to be measured, for example, the occurrence of noise. Where, however, the porous layer is made too thick, then the resultant electrochemical measuring apparatus makes a slower response. Therefore, the asymmetric semipermeable membrane as a whole is desired to have a thickness of 10 to 50 microns or perferably 25 to 35 microns. Further, the thick porous layer should preferably be formed of pores having a diameter of 0.1 to 5 microns.

The asymmetric semipermeable membrane is prepared from, for example, cellulose derivatives such as cellulose acetate, cellulose butylate, and cellulose propionate; polyvinyl alcohol derivatives such as polyvinyl acohol, polyvinyl acetal, and polyvinyl benzal; polyacrylonitrile; polyamide; polyimide; acrylonitrile-vinyl chloride copolymer; polyvinyl chloride; and polysulfone.

The manufacturing method of the asymmetric semipermeable membrane is generally known as disclosed in the following literature:
"Desalination Membranes from Organic Casting Solutions" by Serop manjikian, I & EC Product Reserch and Development vol. 6, No. 1, March (1967), pp 23–32; and "The Structure of Cellulose Acetate Membranes for Reverse Osmosis" by G. J. Gittens, et al, Desalination, 12, (1973), pp 315–332, Elsevier Scientific Publishing Company, Amsterdam.

It is possible to prepare the asymmetric semipermeable membrane from two layers, one formed of smaller pores, and another formed of larger pores. The subject asymmetric semipermeable membrane can be produced by coating an organic casting solution on the porous layer having larger pores. In this case, the asymmetric semipermeable membrane having the two plies of the thick porous layer may be made of the same material or different materials.

Figure 2:
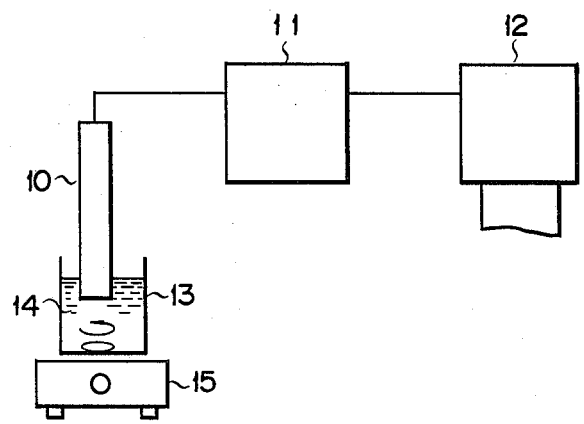
FIG. 2 is a schematic block circuit diagram of the electrochemical measuring apparatus of the invention.

As shown in FIGS. 1B, 1C and 1D, the immobilized enzyme membrane 6 and asymmetric semipermeable membrane 7 are detachably fitted to the electrode section by a seal member 9 such as an O-ring or rubber packing. The enzyme electrode 10 thus constructed is connected, as shown in FIG. 2, to a display device 12 through an amplifier or differentiation circuit 11. The display device 12 may be a recorder, meter or display tube.

The enzyme electrode 10 is dipped in a measurement cell 13 filled with a liquid 14 whose organic content is to be determined. Measurement is carried out while the liquid 14 is agitated by, for example, a magnetic stirrer 15.

The electrochemical measuring apparatus of this invention can be applied by properly selecting an enzyme and an electrode section in the selective quantitative analysis of, organic ingredients contained in a liquid, for example, glucose, galactose, sucrose, uric acid, cholesteral, amino acid, nucleic acid, alcohol, urea, penicillin, NADH, and vitamin. The electrochemical measuring apparatus of the invention is effective particularly for the diagnosis and treatment of diabetes by the analysis of the concentration of glucose is blood or urine. This invention will be more fully understood from the examples which follow.

EXAMPLE 1

An oxygen electrode shown in FIG. 1 was used which comprised a platinum cathode 2, lead anode 3. KOH electrolyte 4 and membrane 5 of Teflon (trademark tetrafluoroethylene manufactured by E. I. Dupont de Nemours and CO. Inc., America) having a thickness of 12 microns. An immobilized glucose oxidase membrane 6 was mounted on said Teflon membrane 5. Further, an asymmetric semipermeable membrane 7 of cellulose diacetate having a thickness of 30 microns was set on the outside of said immobilized glucose oxidase membrane 6, with the thin semipermeable layer component of said membrane 7 exposed to the outside. Said membrane 7 was fixed in place by an O-ring 9. The asymmetric semipermeable membrane of cellulose diacetate had the following permeability, when ultrafiltration was carried out at a pressure of 2 kg/cm$^2$: 1 to 2% for PVP K-90 (molecular weight of 360,000), 1 to 2% for albumin (molecular weight of about 70,000), 99 to 100% for glucose (molecular weight of 180).

The concentration ($2 \times 10^{-4}$ M) of glucose in blood was measured by an electrochemical measuring apparatus provided with the above-mentioned enzyme electrode. Measurement was carried out at a temperature of 37° C. while the blood received in a measurement cell was agitated by a stirrer rotated at a speed of 400 r.p.m.

By way of comparison, three control experiments were carried out with an electrochemical measuring apparatus in which the enzyme electrode was formed of the conventional type. The enzyme electrode used in Control 1 was the type which lacked the asymmetric semipermeable membrane 7 of cellulose diacetate included in the enzyme electrode applied in Example 2. The enzyme electrode used in Control 2 was the type in which a Teflon membrane having a thickness of 36 microns was substituted for the Teflon membrane 5 having a thickness of 12 microns which was used in Control 1 in order to reduce noises. The enzyme electrode used in Control 3 was the type in which a polycarbonate membrane having a thickness of 5 microns was applied in place of the asymmetric semipermeable membrane 7 of this invention. The polycarbonate membrane was formed of pores having an average diameter of 0.03 microns, and indicated the following permeability when ultrafiltration was carried out at a pressure of 2 kg/cm$^2$:
 1 to 2% for PVP K-90,
 4% for albumin,
 98% for glucose,
The results of measuring the concentration of glucose in blood are set forth in Table 1 below.

TABLE 1

|  |  | Example 1 | Control 1 | Control 2 | Control 3 |
|---|---|---|---|---|---|
| Glucose concentration: $2 \times 10^{-4}$M Measured at 37° C. Stirrer rotated at 400 r.p.m. | Difference between current at glucose concentration of $2 \times 10^{-4}$M and current at glucose concentration of 0 | 0.68 microampere | 0.70 microampere | 0.66 microampere | 0.1 microampere |
|  | Response time (98%) | 10-12 sec | 8-11 sec | 50-70 sec | 10-15 sec |
|  | Noise level (N) | <0.01 microampere | 0.09-0.11 microampere | 0.01-0.02 microampere | 0.01-0.02 microampere |
|  | S/N ratio | >68 | 6.4-7.8 | 33-66 | 5-10 |
|  | Durability | Usable for more than 100 days | Immobilized enzyme membrane broken after application of 5 to 15 days | Immobilized enzyme membrane broken after application of 5 to 15 days | Usable for 50 to 60 days |
|  | Stability in measuring the concentration of glucose in whole blood and serum | Sensitivity and response speed did not fall in more than 1000 measurements | Sensitivity and response speed gradually dropped. Noticeable variations appeared in measured data | Sensitivity and response speed gradually dropped. Noticeable variations appeared in measured data | Sensitivity began to fall after about 200 measurements |

Table 1 above shows that Example 1 using the enzyme electrode of this invention made a quick response and indicated an extremely low noise level as less than 0.01 microampere. Moreover, in Example 1 current prominently varied with the concentration of glucose, and the S/N ratio indicated was larger than 68, thus proving high precision measurement. The electrochemical measuring apparatus of this invention has been further found capable of reliably determining even a lower glucose concentration than $3 \times 10^{-6}$ M. As seen from Table 1 above, the immobilized enzyme electrode could be used for more than 100 days without replacement. It was further found that even after the glucose concentration in the human blood and serum was determined more than 1000 times the enzyme electrode of this invention showed little decrease in sensitivity and response speed and was hardly contaminated by, for example, serum protein. The asymmetric semipermeable membrane used with the enzyme electrode of the invention was not plugged with an interfering material such as serum protein, allowing for the easy cleaning of said electrode. A large amount of water contained in the thick porous layer component of the present asymmetric semipermeable membrane does not render the immobilized enzyme membrane dry even when the enzyme electrode was pulled out of a liquid. The above mentioned facts seem to contribute to the elevation of the durability and stability of the enzyme electrode of this invention.

On the other hand, in Control 1, the immobilized enzyme membrane was not covered with such asymmetric semipermeable membrane as used in the invention, resulting in a small S/N ratio and a very low precision of measurement. The enzyme electrode of Control 1 was accompanied with considerable noise, failing to measure a lower glucose concentration than $3 \times 10^{-5}$ M. In Control 2, the occurrence of noise was reduced to substantially the same level as was observed in Example 1, but a response consumed 50 to 70 seconds, a value more than 5 times longer than in Example 1. In both Controls 1 and 2, the immobilized enzyme electrode which was exposed was broken after application of 5 to 15 days.

In Control 3, the immobilized enzyme membrane was covered with a thin (5 microns) polycarbonate layer, and made a response in substantially as short a time and was accompanied with substantially as little noises as in Example 1. In Control 3, however a far smaller signals was generated than in Example 1 as measured on the basis of the same glucose concentration, and consequently indicated a small S/N ratio, or a low precision of measurement. Control 3 had such durability that the immobilized enzyme membrane could be applied without replacement for 50 to 60 days and did not drop in sensitivity and response speed until it was used about 200 times. The reason why Control 3 had a considerably lower durability and stability than in Example 1 is assumed to be that the polycarbonate layer was not an asymmetric semipermeable type.

EXAMPLES 2-5

In these Examples, the electrode section and asymmetric semipermeable membrane were assembled in different manners from that which was used in Example 1. In Example 2, the same oxygen electrode as in Example 1 was used. In Example 3 a hydrogen electrode was applied. In Example 4 a carbon dioxide electrode was used. In Example 5, a hydrogen peroxide electrode was applied. Three kinds of asymmetric semipermeable membranes were used: A (a polysulfone membrane); B (a cellulose acetate membrane prepared by controlling the evaporation time of a solvent to 15 seconds); and C (a cellulose acetate membrane prepared by controlling the evaporation time of a solvent to 30 seconds). Membrane A was used in Example 3, membrane B in Example 4, and membrane C in both Example 2 and 5. The permeability of the respective membranes A, B, C is shown in FIG. 3, which further indicates the permeability of a polycarbonate membrane D as a control having a thickness of 5 microns and an average pore diameter of 0.03 micron (pore density: $6 \times 10^8$ pore/cm$^2$), and a polycarbonate membrane E also as a control having a thickness of 5 microns and an average pore diameter of 0.05 (pore density: $6 \times 10^8$ pore/cm). The permeability of the five membranes A, B, C, D, E was determined with respect to 0.1% aqueous solution of glucose (MW 180), PEG 1000 (MW 1000), PEG 2000 (MW 2000), PEG 6000 (MW 7500), PEG 20,000 (MW 20,000), bovine albumin (MW 67,000) and PVP K-90 (MW 360,000) when said solutions were subjected to an ultrafiltration at a pressure of 4 kg/cm$^2$, with the average flow rate of said solutions over the membrane surface set at 0.4 to 1 m/sec. The determination was carried out by the formula: concentration of a liquid permeating the membrane $\times$ 100/concentration of the original liquid.

Table 2 below shows the materials and durability of the enzyme electrodes and measured organic materials.

Throughout Examples 2 to 5, the enzyme electrode coated with an asymmetric semipermeable membrane made a response in a time of only 1 to 5 seconds longer than that which was without an asymmetric semipermeable membrane, and moreover could be applied in a very stable condition for a long time.

TABLE 2

| | | Example 2 | Example 3 | Example 4 | Example 5 |
|---|---|---|---|---|---|
| Enzyme Electrode | Electrode section | O$_2$ electrode coated with Teflon layer | H$^+$ electrode | CO$_2$ electrode | H$_2$O$_2$ electrode |
| | Immobilized enzyme membrane | Immobilized cholesterol oxidase membrane | Immobilized urease membrane | Immobilized uricase membrane | Immobilized glucose oxidase membrane |
| | Asymmetric semipermeable membrane | membrane C | membrane A | membrane B | membrane C |
| Material detected | | Cholesterol | Urea | Uric acid | Glucose |
| Durability in analyzing the whole blood | | Even when applied 500 to 1000 times, the enzyme electrode showed no decrease in a response speed and maintained 95% sensitivity | Same as left | Same as left | Even when applied more than 1000 times, the enzyme electrode did not fall in sensitivity and response speed |
| Remarks | | Applicable for 20 to 40 days at 25° to 37° C. | The enzyme electrode maintained more than half the original activity even when applied for 30 days at 25° to 37° C. | Same as left | Stably applicable for more than 100 days at 25° to 37° C. |

Tests were made of the long term stability of the enzyme electrode of Example 1 and the enzyme electrode of Control 1 free from an asymmetric sempermeable membrane, the results being set forth in FIG. 4.

The tests were carried out as follows. The sample enzyme electrodes were stored in a buffer solution having a pH value of 7.7 at 23° to 28° C. Measurement was made of a fixed concentration of glucose in a liquid to be measured, for example, blood at 37° C. at an interval of several days. Determination was made of the ratio $\Delta It/\Delta Io$, where $\Delta Io$ is the current measured on the first day of the test and $\Delta It$ is the current measured on each succeding day. The plotted points given in FIG. 4 respectively denote an average of 5 to 15 measurements. The enzyme electrode of this invention was applicable for more than 100 days without replacement of the asymmetric semipermeable membrane, and indicated extremely well with respect to variations in measured values. In contrast, the enzyme electrode free from an asymmetric semipermeable membrane showed a sharp decline in the measured current $\Delta It$. On the 15th day of application, the immobilized enzyme membrane itself was broken with the resultant failure to make measurements.

An electrochemical measuring apparatus embodying this invention which is prominently improved in sensitivity and responsiveness is applicable to the selective quantitative analysis of an organic ingredient such as glucose, galactose, sucrose, uric acid, cholesterol, amino acid, nucleic acid, alcohol, urea, penicillin, NADH, and vitamin, wich is contained in a liquid to be measured, for example, blood. The present electrochemical measuring apparatus is particularly effective for the medical diagnosis and treatment of diabetes by analyzing the concentration of glucose contained in blood or urine.

What we claim is:

1. An electrochemical measuring apparatus provided with an enzyme electrode which comprises an electrode having adjacent thereto a filter membrane which is permeable to a material to be detected but impervious to a material of larger particle size than the material to be detected, a separate immobilized enzyme membrane deposited on said filter membrane, and an asymmetric semipermeable membrane mounted on the immobilized enzyme membrane, said asymmetric semipermeable membrane being essentially formed of an outer thin semipermeable layer of a thickness less than 1 micron exposed to contact with a liquid to be measured and an inner thick porous layer within said thin semipermeable layer, whereby the concentration of an organic ingredient contained in said liquid to be measured is determined by utilizing the reaction of the enzyme set in said immobilized enzyme membrane.

2. The apparatus according to claim 1, wherein the asymmetric semipermeable membrane is impervious to more than 80% of a material having a molecular weight of 20,000 and permeable to more than 70% of a material having a molecular weight of 1,000.

3. The apparatus according to claim 1, wherein the asymmetric semipermeable membrane has a thickness of 10 to 50 microns.

4. The apparatus according to claim 1, wherein the asymmetric semipermeable membrane is an integral material in which the fine pores of the thin semipermeable layer are arranged adjacent to the coarse pores of the thick porous layer in the direction through the thickness of said asymmetric semipermeable membrane.

5. The apparatus according to claim 1, wherein the asymmetric semipermeable membrane is formed by laminating a separate thick porous layer having coarse pores with a separate thin semipermeable layer having fine pores, such that the latter layer is exposed to the outside.

6. The apparatus according to claim 1, wherein the electrode is an oxygen electrode which essentially comprises:
   an electrode cylinder;
   a cathode and anode received in said electrode cylinder;
   an electrolyte filled in a space defined between said cathode and anode; and
   a filter membrane disposed near the cathode to constitute the sensitized plane of the electrode.

7. The apparatus according to claim 1, wherein the immobilized enzyme membrane is formed by physically or chemically depositing glucose oxidase on a substrate.

* * * * *

UNITED STATES PATENT AND TRADEMARK OFFICE
CERTIFICATE OF CORRECTION

PATENT NO. : 4,388,166
DATED : June 14, 1983
INVENTOR(S) : Shuichi Suzuki et al.

It is certified that error appears in the above-identified patent and that said Letters Patent is hereby corrected as shown below:

On the title page:

"[22] Filed: May 15, 1982" should read -- [22] Filed: -- March 15, 1982 --.

Signed and Sealed this

Sixth Day of September 1983

[SEAL]

Attest:

GERALD J. MOSSINGHOFF

Attesting Officer     Commissioner of Patents and Trademarks